(12) United States Patent
Dalton

(10) Patent No.: US 7,763,056 B2
(45) Date of Patent: Jul. 27, 2010

(54) CERVICAL COMPRESSION PLATE ASSEMBLY

(76) Inventor: Brian E. Dalton, 333 State St., Erie, PA (US) 16507

( * ) Notice: Subject to any disclaimer, the term of this patent is extended or adjusted under 35 U.S.C. 154(b) by 1906 days.

(21) Appl. No.: 10/642,976

(22) Filed: Aug. 18, 2003

(65) Prior Publication Data

US 2005/0043732 A1   Feb. 24, 2005

(51) Int. Cl.
- A61B 17/66 (2006.01)
- A61B 17/58 (2006.01)
- A61B 17/70 (2006.01)
- A61B 17/80 (2006.01)
- A61B 17/86 (2006.01)

(52) U.S. Cl. ............... 606/282; 606/70; 606/71; 606/280; 606/286; 606/288; 606/290; 606/902

(58) Field of Classification Search ............. 606/69–73, 606/280–299, 902–907, 60; 623/17.13
See application file for complete search history.

(56) References Cited

U.S. PATENT DOCUMENTS

| | | | | |
|---|---|---|---|---|
| 5,057,111 A | * | 10/1991 | Park | 606/69 |
| 5,458,642 A | * | 10/1995 | Beer et al. | 623/17.13 |
| 5,616,142 A | * | 4/1997 | Yuan et al. | 606/61 |
| 5,735,853 A | * | 4/1998 | Olerud | 606/71 |
| 5,800,433 A | | 9/1998 | Benzel et al. | |
| 6,066,142 A | * | 5/2000 | Serbousek et al. | 606/96 |
| 6,306,136 B1 | | 10/2001 | Baccelli | |
| 6,328,738 B1 | | 12/2001 | Suddaby | |
| 6,402,756 B1 | | 6/2002 | Ralph et al. | |
| 6,695,846 B2 | * | 2/2004 | Richelsoph et al. | 606/71 |
| 7,008,427 B2 | * | 3/2006 | Sevrain | 606/71 |
| 2002/0111630 A1 | | 8/2002 | Ralph et al. | |
| 2002/0188296 A1 | | 12/2002 | Michelson | |
| 2003/0114856 A1 | * | 6/2003 | Nathanson et al. | 606/70 |

* cited by examiner

Primary Examiner—Thomas C Barrett
Assistant Examiner—Sameh Boles
(74) Attorney, Agent, or Firm—Carothers & Carothers

(57) ABSTRACT

A cervical compression plate assembly having screw receiving elements at opposite ends that are configured for engaging bone fixation screws extending from respective vertebral elements. The assembly permits the distance between the screw receiving elements at opposite ends to be shortened but prevents the distance from increasing. A spring mechanism is housed within the plate assembly and is configured for continuously urging the screw receiving elements at opposite ends together for thereby providing continuous compressive loading on bone graft material disposed between the vertebral elements.

18 Claims, 7 Drawing Sheets

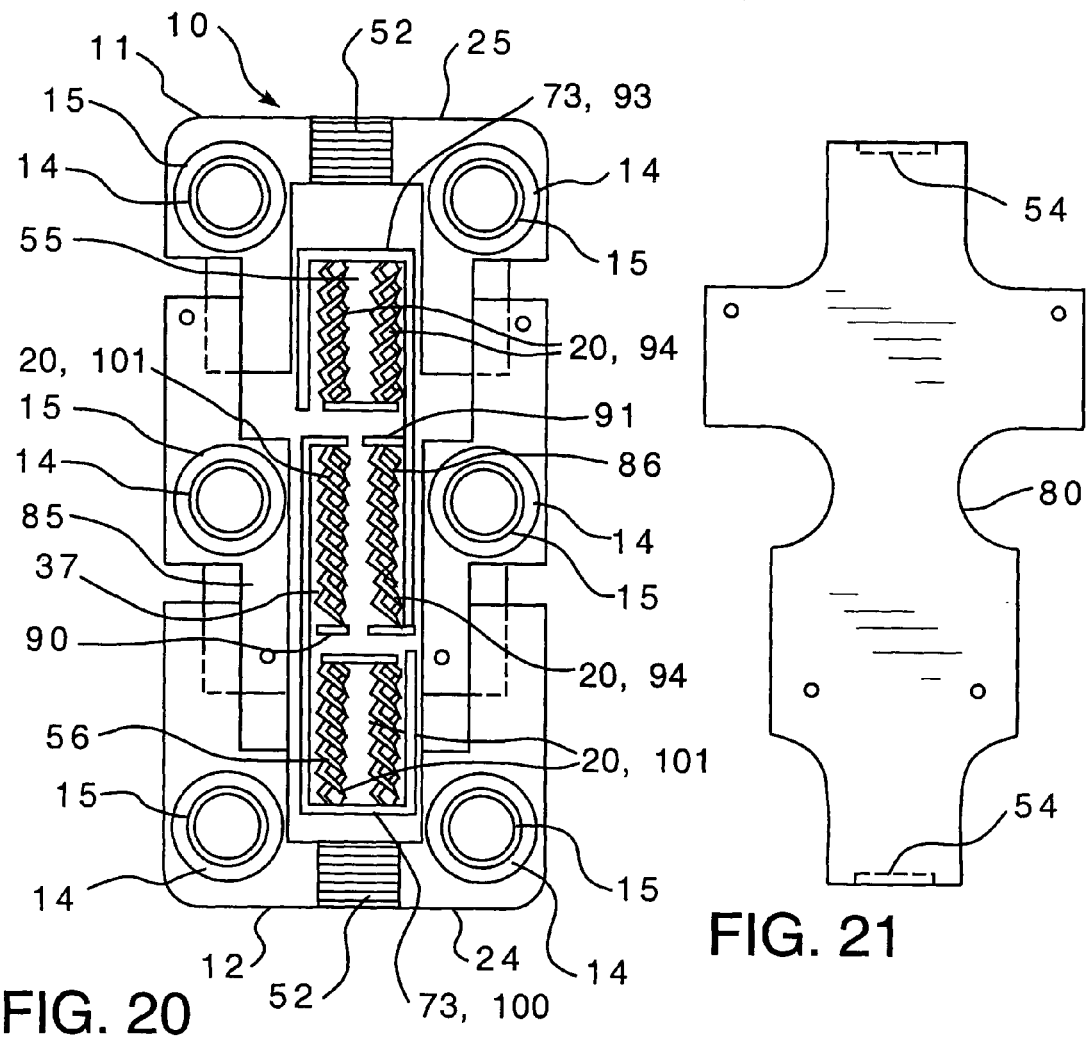
FIG. 20
FIG. 21
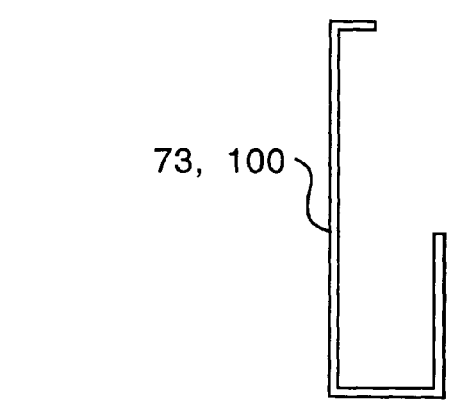
FIG. 22
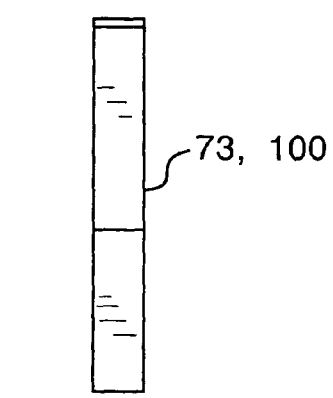
FIG. 23

CERVICAL COMPRESSION PLATE ASSEMBLY

BACKGROUND OF THE INVENTION

This invention relates to spinal surgery, and more particularly to an anterior cervical fusion compression plate.

The human spinal column is a structure consisting anteriorly of the individual vertebral bodies and the intervertebral discs. The posterior aspect of the spine consists of joints and ligaments which primarily provide a tension band for the spine. The anterior column tends to have characteristic curvatures while viewed from the sagittal plane (from the side) in the cervical, thoracic and lumbar areas, the cervical area having a lordotic or forward bow curve. These various curves are important to be maintained since they allow the spine to have sagittal balance and be agile through normal range of motion when stressed by the various contractions of muscles, etc. Disc degeneration which can lead to disc herniation as well as spur formation usually causes a lessening of the normal cervical lordosis and may lead to significant pain involving the neck as well as radicular pain due to nerve root compression. Tumors, disease, trauma and degeneration are all factors which can lead to spinal pathologies requiring fusion.

The usual approach to diseases of the spine, when they do not respond to conservative therapy, includes operation. Operations have approached the cervical spine with either an anterior approach, involving the vertebral bodies and discs, or a posterior approach, which allows for decompression of the nerve roots as they exit the spinal foramina and a very limited degree of discectomy via laminotomy. For derangements of spinal alignment, large herniated discs, compression of the spinal cord due to discs or spurs or fracture, the anterior approach is generally favored. The anterior approach also allows for correction of spinal deformity. When the intervertebral disc is removed or offending bone fragments are removed, the cavity which is created in this surgery is generally filled by a graft material. Graft materials have been procured from the patient themselves (autograft) as well as from bone bank bone (allograft) and then in certain circumstances synthetic materials are used, such as PEAK, corral and synthetic porous materials.

A number of factors have been identified as being necessary to achieve a solid bony fusion across an operated site. These factors include: 1) relative immobility across the operative site, to limit movement of the graft material relative to the surrounding metabolically active bones, 2) compressive loading force across the graft site, 3) healthy metabolically active bone, and 4) adequate blood supply. Regarding the second factor, compressive loading force across the graft site, this compressive force allows the avoidance of gapping between the graft material and the metabolically active bone which is attempting fusion with the graft material. The mechanism of bone formation with grafting, termed "creeping substitution" causes to a small degree loss of graft material, thus possibly forming a gap. This is due to a resorptive phase in the bone formation mechanism. This bone resorption can result in gaps between the bone graft and the metabolically active bone and if the juxtaposition of graft and surrounding bone is not close enough, or if there cannot be a mechanism by which the level can compress together and maintain that close contact, a pseudoarthrosis or false fusion can occur.

Studies have been performed to evaluate cervical fusions, and specifically studies have looked at cervical discectomy with fusion when performed at one, two and three levels. It has been found that the fusion rate at a one level in the spine is much higher than at a second level if done at the same sitting, and a third if done at the same sitting is lower than the second and first levels. This is felt to be due to an inability to maintain adequate stabilization of the spine during postoperative healing at the second and third levels as compared to the first level.

In an effort to enhance stability in post surgical cervical fusion patients, anterior cervical plating has been utilized. In these constructs, the anterior cervical plating system is rigidly affixed to the bones above and below each level fused in an effort to maintain stability. The compression across the graft is provided by slightly over sizing the graft within the gap created by removal of disc and the resultant compression is provided by the counteractive force of the stretched spinal ligaments.

When considering a rigid anterior cervical plating system, a certain amount of compressive force can be placed across the graft during the initial placement of the plate by angling the screws above and below the level of the graft, and lagging the plate to the vertebral body. In this instance, the stored compression may not be enough to allow for the process of creeping substitution described earlier. The plate then will begin to act as a fixed cantilever and actually may allow the surrounding bone to be held apart from the graft material. The process of creeping substitution may then allow gaps to form thereby leading to pseudoarthrosis. This ultimately can lead to pain and/or deformity and require further surgeries. This is termed a distraction pseudoarthrosis.

Other cervical plating systems have been introduced in an attempt to prevent this distraction pseudoarthrosis by allowing the vertebral bodies to move towards each other as needed during the fusion process. This has generally been done by allowing bone screws to be free to rotate, swivel, slide or angulate independent of the anterior cervical plate itself. These screws are free to carry out these actions despite the fact that they are fixed from backing out of the plate. This does allow some freedom of motion of the vertebrae to move toward each other during the fusion process but does lead to a degree of multi-directional instability that is contrary to the purpose of the anterior cervical plating hardware, which is to provide increased stability.

Yet another approach to addressing the issue of providing compressive force across the graft has involved a plating system by which a bar is attached to each vertebral body and each of the bars can slide on a pair of rods. These constructs do allow movement of the bone across the graft surface, however they do sacrifice stability in the sense that the vertebral bodies attached to the sliding bars can easily slide away from the graft as well, particularly when the patient in the supine position when the head is not weighting the graft. These types of systems sacrifice stability in the sagittal plane to allow for the compressive force generated by the head when the patient is in the upright position. The second issue is the compressive force that is provided across the graft is provided solely by the weight of the patient's head and therefore these systems are entirely ineffective if the patient is in the supine position, and in fact, if the patient is in the supine position and the head is levered around an object such as a cervical collar, it can actually be a distractive force across the fusion site which is definitely contrary to the purpose of the surgery.

U.S. patent application Publication No. US 2002/0188296 teaches a plate that allows not only for the sliding of the plate from an elongated to a collapsed status, a process termed by the inventor as dynamization, but the plate also does not allow for challenged distraction. This plate would therefore allow a compressive load to be applied to the graft within the physiologic range (weight of the head), and if the graft dissolves to a degree, the plate allows the vertebral bodies to move towards each other, but not away. This prior art plate also teaches what the inventor calls "active dynamization" by which the plating system is forced to store energy to induce shortening of the fusion construct should the opportunity present, primarily due to the maneuvers discussed herein before, including over sizing the graft and diverging the screws. This concept may be considered as "dynamization", but the designation of this concept as being "active" dynamization would, in the view point of the present inventor, be inaccurate as there is no active element for applying compressive loading.

The limitations of this prior art plating system are the same as with other subsidence systems in that the compressive load across the graft is supplied by the patient's head and is only present at the time when the patient is upright. This force is very readily removed as soon as the patient is in the supine position. This prior art plate however does not have the negative that is shared by other systems of the prior art such as found in U.S. Pat. No. 6,402,756, as well as in U.S. Pat. Nos. 5,616,142, 5,800,433 and U.S. Publication No. 2002-0111630, which have distraction across the graft site in the supine position. U.S. Pat. No. 6,328,738 discloses another prior art plate which, similar to the other prior art mechanisms, would prevent distraction across the graft site, but is ineffective in providing any active compression.

SUMMARY OF THE INVENTION

From the prior discussion, it is realized that there exists therefore a need for an improved anterior cervical plating system that is sufficiently rigid to maintain the alignment of the vertebral bodies relative to the level to be fused, capable of maintaining, as well as inducing, a compressive load across the fusion site, and capable of allowing for the motion of the vertebral bodies surrounding the level of fusion to maneuver towards each other in an effort to close any gaps between the metabolically active bone fusing as well as the bone graft that occurs due to the process of creeping substitution. This has to occur while the system is simultaneously preventing motion in all other planes. Furthermore, the system must be capable of maintaining physiologic compressive load across the fusion site independent of the patient's position while at the same time limiting any distraction which may occur in less stable systems when the patient is in the supine position, thus avoiding a distraction pseudoarthrosis.

The present invention provides an anterior cervical plating system possessing the capability of true active dynamization. This term describes the ability of the plating system to generate, as well as maintain, a compressive force across the graft at all times. The compressive force is generated by an integral mechanism that stores energy that effectively causes this compression. The plate system of the present invention is substantially simpler to fit and affix to the human spine than other dynamic systems since there is no modularity of the system. Each plate has all dynamic components and mechanisms already assembled in preset sizes so that the surgeon merely needs to measure and affix the appropriate size plate. The elements which slide with respect to each other cannot be detached and portions of these plates of the present invention cannot be lost as the internal mechanism thereof is entirely self-contained within the plate, and is not available for disassembly by the operator.

The plate of the present invention is fixed at two or more cervical vertebrae with the aid of a pair of bone fixation screws at each level of fixation of the spine and the individual components of the plate are able to slide relative to each other but only in one direction to allow closure of the spaces between the bone screws, allowing a decreasing distance between the vertebrae relative to each other.

Furthermore, the bone fixation screws are locked to the plate by a self-contained locking mechanism. This locking mechanism allows for the multi-directional placement of a screw, but once the screw is fully seated, it is rigidly locked in that trajectory, also, the screw design allows for the screws to be lagged through the plate to the vertebrae allowing a very close intimate fixation of the cervical plating system to the anterior aspect of the spine. A drawback of the systems of the prior art is that the mechanism by which the screw fixes to the plate requires the screw to be intimately machine threaded into the plate and does not allow for lagging of the plate to the vertebrae.

More specifically, the cervical compression plate assembly of the present invention provides screw receiving elements at opposite ends thereof which are configured for engaging bone fixation screws extending from respective vertebral elements. A means is provided for permitting the distance between the screw receiving elements at opposite ends of the plate to be shortened, but preventing this distance from increasing. The improvement of the present invention resides in a compression spring means housed in the plate assembly and configured for continuously urging the screw receiving elements at opposite ends of the plate assembly together for thereby providing continuous compressive loading on bone graft material disposed between the vertebral elements.

This ability to permit the movement of adjacent vertebral bodies towards one another is referred to herein as dynamization. Dynamization may be passive, which describes the plate assemblies of the prior art wherein the prior art plate assemblies allow the plate assembly to shorten when a compressive load is applied along the axis or sagittal axis of the plate. However, dynamization is termed as being "active" in the plate assembly of the present invention wherein the plating system stores energy which induces shortening of the plate if the opportunity is presented, such as with creeping substitution. More importantly, this stored compressive force can maintain a physiologic compressive stress across the graft which has been shown to have a beneficial effect on the healing of bone.

The cervical compressing plate assembly of the present invention also includes a screw locking mechanism for locking the screws to the plate assembly and also permits the screws to be lagged to the plate assembly due to the existence of screw receiving elements in the plate assembly which include screw head seats configured for seating and locking the heads of the bone fixation screws at different attitudes. The screw locking mechanism includes pressure fit rings in the screw receiving elements for engaging and locking the self tapping threaded shanks of the bone fixation screws in preselected angles of attitude. Locking caps may be alternatively or supplementally provided to also lock the screws at preselected attitudes.

The spring means provided in the plate assembly of the present invention may be or include either a tension spring or a compression spring to provide the active compression. When provided in the form of a tension spring, it may be a wire spring placed under tension or a coil or ribbon spring placed under tension. When provided in the form of a compression spring, the spring may be in the form of a coil spring or ribbon spring. When provided in the form of a wire tension spring, it is also desirable to provide a torque drive for adjusting the tension applied to the wire. The spring means is intended to include other spring elements which may be substituted, such as fluid cylinders, hydraulic piston and cylinder combinations, and compressible and stretchable solids such as polymeric foams.

In the plate assembly of the present invention, a spacer is provided and disposed between the screw receiving elements at opposite ends of the plate assembly for initially preventing the distance between the screw receiving elements at opposite ends from being shortened by the compression spring means before application of the plate assembly to the spine. Thus the plate assembly of appropriate size is selected and secured to the spine and then the spacer or spacers are removed to thereafter continually apply the compressive loading.

BRIEF DESCRIPTION OF THE DRAWINGS

Other objects and advantages appear hereinafter in the following description and claims. The accompanying drawings show, for the purpose of exemplification, without limiting the invention or the appended claims, certain practical embodiments of the present invention wherein:

FIG. 20 is a view in front elevation illustrating a variation of the cervical compression plate assembly shown in FIG. 17 with modifications for two-level application;

FIG. 21 is a view in front elevation of the cover plate for the assembly shown in FIG. 20;

FIG. 22 is a view in front elevation of one of the spring containment housings for the embodiment illustrated in FIG. 20;

FIG. 23 is a view in right side elevation of the spring containment housing shown in FIG. 22.

DETAILED DESCRIPTION OF THE PREFERRED EMBODIMENTS

Figure 1:
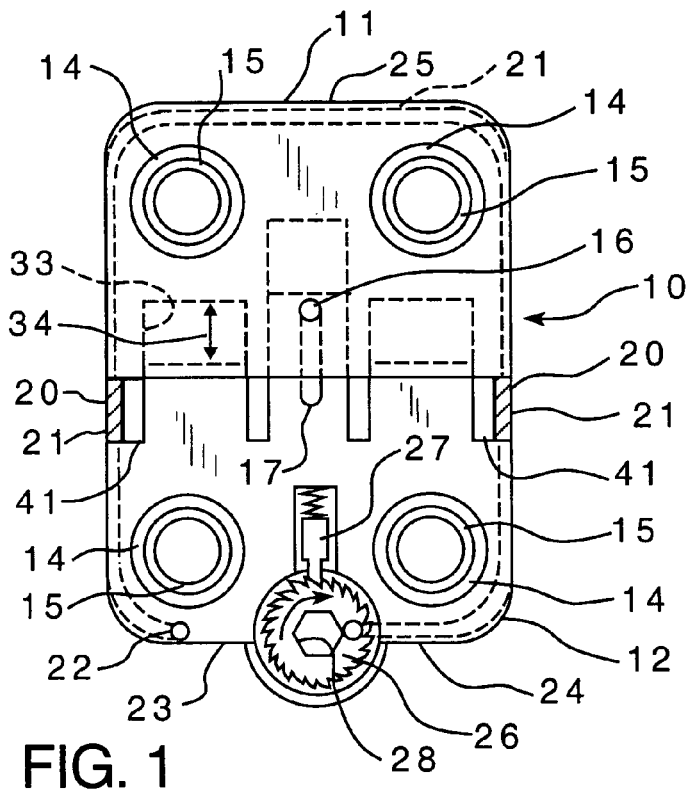
FIG. 1 is a view in front elevation of one embodiment of the cervical compression plate assembly of the present invention.
Figure 2:
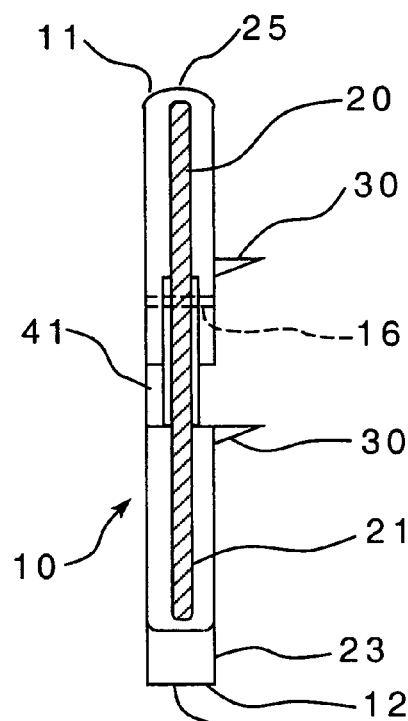
FIG. 2 is a right side view in elevation of the cervical compression plate assembly of FIG. 1.
Figure 3:
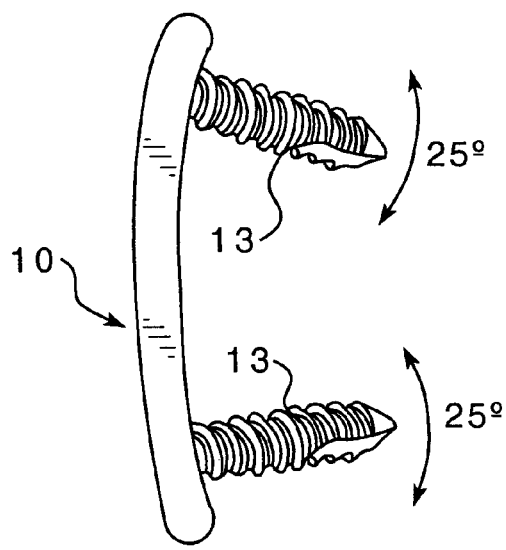
FIG. 3 is a schematic view in side elevation of a cervical compression plate assembly of the present invention illustrating sagittal curve to allow the plate assembly to fit with the contour of the cervical spine.
Figure 4:
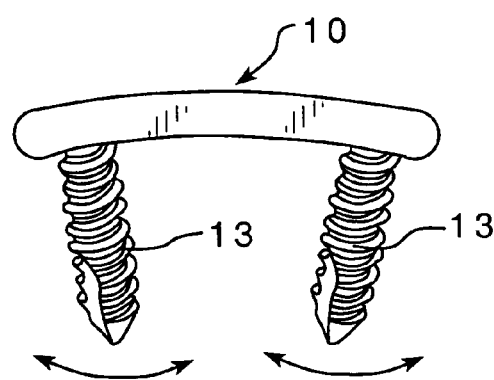
FIG. 4 is a bottom or top schematic end view of a cervical compression plate assembly of the present invention for illustrating coronal curve to allow the plate assembly to fit with the contour of the cervical spine.

Referring first to the embodiment illustrated in FIGS. 1 and 2, the cervical compression plate assembly 10 is provided with screw receiving elements 11 and 12 at opposite ends thereof which are configured for engaging bone fixation screws 13, illustrated in FIGS. 3 and 4, extending from respective vertebral elements of the human cervical spine. The screw receiving elements 11 and 12 in this embodiment are each respectively provided with spaced identical screw head seats 14 configured for seating the heads of the bone fixation screws at different attitudes. The bone fixation screws 13 are provided with heads that have underside perimeter edges which engage the seats 14. Seats 14 are annular concave so that the screws 13 may be received within and on seats 14 at different desired attitudes or angles. This permits the surgeon to lag cervical compression plate assembly 10 securely to the cervical spine as desired. Accordingly, the angle by which the bone fixation screws 13 pass through the plate assembly 10 can be varied according to the surgeon's wishes. There is a choice of approximately 25° of arc that the surgeon can utilize in placement of each screw as is illustrated in FIGS. 3 and 4.

Within each seat 14 is provided a self contained pressure fit bushing ring 15. The bone fixation screws 13 are self tapping and when inserted through the passages in plate assembly 10 as provided by the respective seats 14 at respective desired angles relative to plate assembly 10, the self tapping threads of bone fixation screws 13 not only self tap into pre-drilled holes into the underlying vertebrae, but the threads thereof also engage and self tap pressure fit rings 15 to thereby affix each screw to the plate assembly 10 at its respective predesignated attitude. As an alternative bushing ring 15 may have internal threads to engage and fix the screw shank at the preset angled attitude. Also the seat 14 may be roughened to engage and fix the position of the screw head.

The distance between screw receiving elements 11 and 12 at opposite ends of cervical compression plate assembly 10 may be shortened, but this distance is prevented from increasing. In this embodiment, the distance is prevented from increasing due to the interrelationship of dowel pin 16 as confined within slot 17 which limits the relative movement between screw receiving elements 11 and 12. Additional limitation to prevent this distance from increasing is also provided by the particular spring means or element 20 housed within the cervical compression plate assembly 10. In this embodiment this compression spring means, which is configured for continuously urging the screw receiving elements 11 and 12 at opposite ends together, is provided in the form of a compression tension wire 21 that has elastic characteristics whereby the tension of the wire will not drop too precipitously. For example, this tension wire may be made of stainless steel which has a relatively high Young's constant. Other suitable materials for the tension wire 21 may be substituted.

The spring wire 21 is secured at one end 22 to the housing 23 for the lower plate 24 of the assembly 10. The wire then passes along the perimeter of the assembly 10 as illustrated through a passage in the upper end of upper plate 25 of assembly 10 and then on around the perimeter of assembly 10 where the other end of the tension wire 21 is secured to tension rachet gear 26. Gear 26 is received within the housing 23 for rotation in the clockwise direction only as indicated by the arrow in FIG. 1. Ratchet gear 26 is prevented from turning in the counterclockwise direction by spring loaded pawl 27 which engages the ratchet teeth of gear 26 under spring bias and thereby prevents the gear from turning in the counterclockwise direction due to the configuration of the teeth for gear 26. Ratchet gear 26 is provided with a central hex drive socket 28 for engagement by a torque limiting screw driver having a complimentary tip whereby the ratchet gear 26 may be turned clockwise to the extent desired by the surgeon to provide the appropriate compression between screw receiving elements 11 and 12. Accordingly, the wire spring 21 is tightened in a manner quite similar to a tuning of a guitar string. As is the case with all embodiments of the cervical plate assembly of the present invention, the compression spring means 20 is configured for continuously urging screw receiving elements 11 and 12 at opposite ends of the assembly 10 for thereby providing continuous compressive loading on bone graft material disposed between the vertebral elements being stabilized.

As previously explained, the screws 13 are locked in position with respect to plate assembly 10 by means of pressure fit rings 15. However, as an alternative, the seats 14 may be provided with threaded sides for cooperatively receiving screw head lock nuts (not shown) for respectively clamping against respective screw heads seated therein for thereby locking the screws 13 at the selected attitudes.

The plate assembly 10 will be provided in a variety of lengths according to the patient's needs. For the purposes of visualization only, the plate assembly 10 in its combined form as shown in FIGS. 1 and 2 might be provided in a thickness of approximately ⅛ of an inch and with a width of approximately 23/32 inches. The plate assembly 10 would then be provided in varying widths that would vary in increments of 1 to 2 mm to accommodate varying anatomies. For overall length the plate assembly 10 might conceivably start at a minimum length of 25 mm and extend to 120 mm or more. Again, the surgeon would preselect the proper pre-fit size for the particular anatomy. At approximately a length of 38 mm, the plates would be provided to have three sets of holes or screw passages, or three sets of screw receiving elements 11 and 12 instead of the two sets illustrated.

The plate assembly 10 may be, and preferably is, provided with a sagittal curve as illustrated in FIG. 3. For example, this sagittal curve might typically be a 9" sagittal curve. The plate assembly 10 may also be provided with a coronal curve, for example of 2.5", as illustrated in FIG. 4 to allow the plate assembly to fit with the contour of the cervical spine. In addition, as is best 20 illustrated in FIG. 2, end plate guides 30 protrude from the back side of the plate assembly 10 just below and above the screw receiving elements 11 and 12 to permit the plate assembly 10 to be properly aligned with the vertebral body prior to fastening the plate assembly 10.

Once the plate assembly is affixed to the anterior aspect of the spine, a compression load is applied by the surgeon by the way of a torque screwdriver applied to ratchet gear 26 for clockwise turning and this therefore applies and maintains compressive force across the fusion level. This compressive force is maintained independent of the patient's position due to stored energy within the torqued wire 21 and will last far longer than the stored compressive loads placed by surgeons at the time of surgery by stretching the spinal ligaments by the over sizing of the bone graft and by divergence of the upper and lower screw pairs as previously explained in the background with regard to the prior art.

Figure 5:
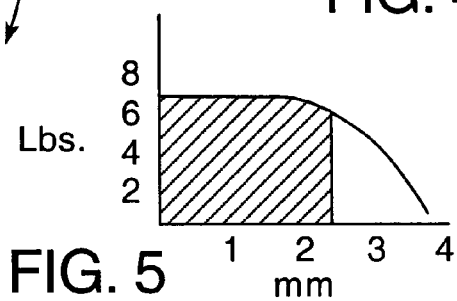
FIG. 5 is a graphical illustration of the elastic characteristics of the compression cable spring used in the cervical compression plate assembly of FIGS. 1 and 2.

The upper and lower screw receiving elements 11 and 12 may converge or slide together toward each other due to the fact that they are respectively provided in separate upper and lower plate portions 25 and 24 of assembly 10 which have gapped inter-sliding parts. Lower plate 24 is provided with two male protrusions 32 which are slidably received and guided within female guides 33 of upper plate 25. Sufficient gapping 34 is provided between these elements to permit compressive loading on bone graph material and thereby provides the active dynamization to maintain a compressive force across the fusion level with the occurrence of creeping substitution. This configuration of the present invention permits continuous contact between surrounding bone and the bone graft at all times despite absorption of the bone that might occur with creeping substitution, and if challenged, resists any forces that would allow distraction across the fusion site by elongation of the plate. Accordingly, the tension wire spring 21 of the cervical plate assembly 10 provides a correctable subsidence zone indicated by the hatched area 40 of the graphical illustration of FIG. 5. Thus as illustrated in the graph, for one to approximately 2.5 mm of subsidence, the plate assembly 10 maintains a relatively constant compression load of 8 to 6 pounds, depending upon the tension of the wire 21 as preselected by the surgeon. Accordingly, the plate assembly 10 is capable of compensating for 2.5 mm of subsidence and in so doing will close the small gaps between the upper and lower plates 25 and 24. Since the screw trajectories are locked relative to the plate assembly 10, the plate assembly 10 may be truly lagged to the cervical vertebrae and thereby locked in their respective trajectories as lagged. Accordingly, the compressive load is assured to be directly and appropriately applied to the subsiding vertebrae and the multi-directional instability seen in plating systems of the prior art is eliminated.

The plate assembly 10 is also provided with pre-positioned spacers 41 which are positioned within the gaps formed between the upper and lower plates 25 and 24. These spacers prevent the upper and lower plates 25 and 24 from converging toward each other until the assembly 10 has been surgically applied. After the plate assembly 10 has been fully seated and secured to the anterior aspect of the cervical spine, the spacers are then removed to permit the plate to immediately apply compressive loading. It can readily observed that if the spacers 41 were removed prior to application, the plate assembly 10 would collapse upon itself.

Figure 6:
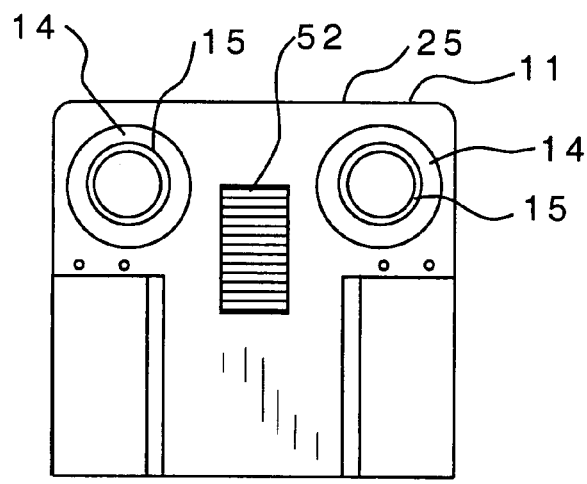
FIG. 6 is a front view in elevation of the upper plate portion of another embodiment of the cervical compression plate assembly of the present invention.
Figure 9:
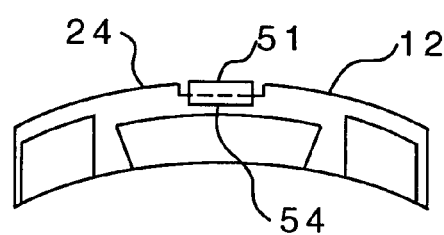
FIG. 9 is a top end view of the lower plate shown in FIG. 8.
Figure 7:
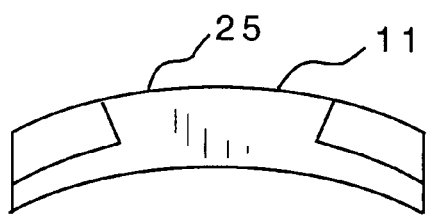
FIG. 7 is a bottom end view of the upper plate shown in FIG. 6.
Figure 8:
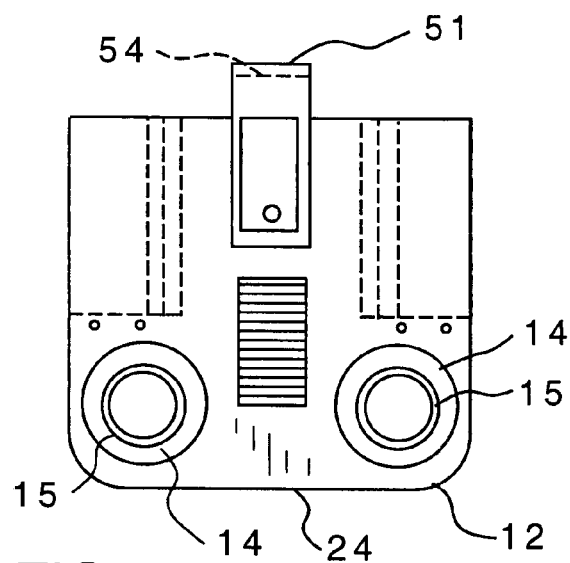
FIG. 8 is a front view in elevation of the bottom plate for combination with the upper plate shown in FIG. 6 to provide an alternate embodiment of the cervical compression plate assembly of the present invention.
Figure 10:
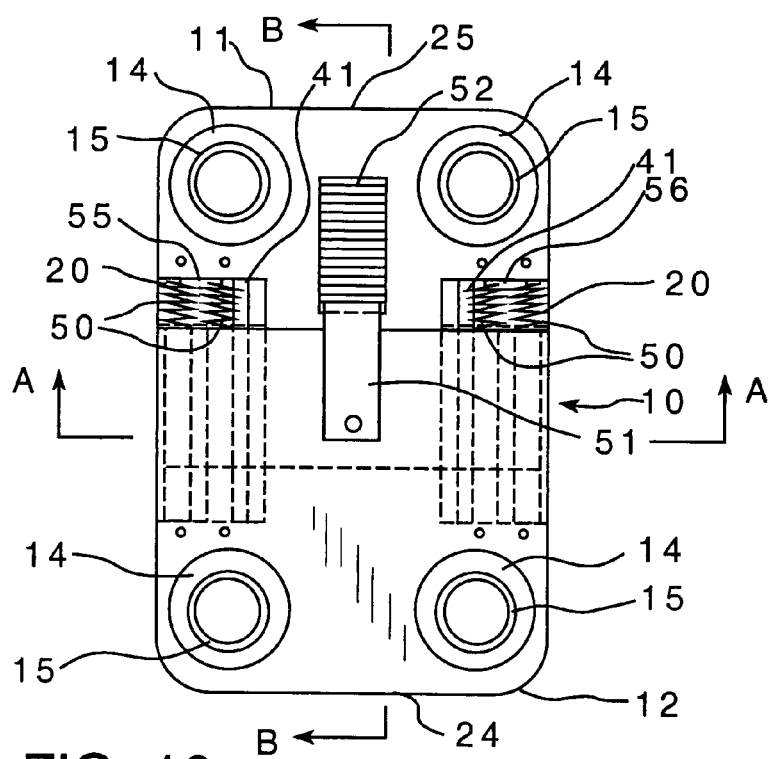
FIG. 10 is a view in front elevation illustrating the embodiment of FIGS. 6, 7, 8 and 9 in combined form.
Figure 12:
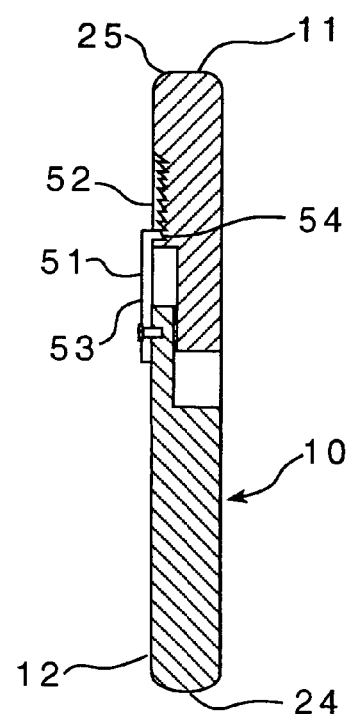
FIG. 12 is a right side cross sectional view in elevation of the assembly shown in FIG. 10 as seen along section line B-B.
Figure 11:
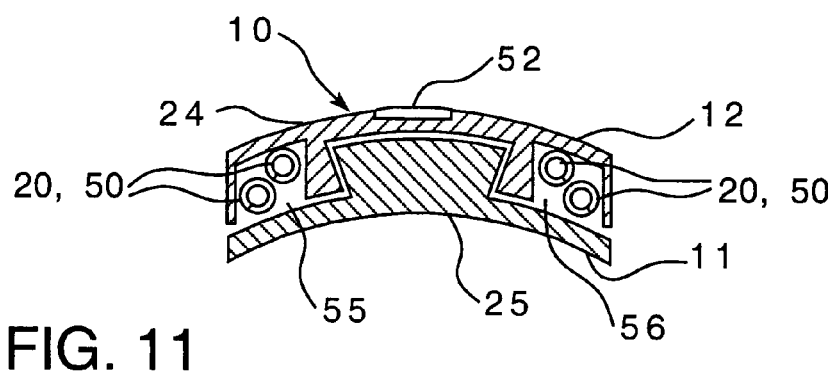
FIG. 11 is a mid cross sectional view of the assembly shown in FIG. 10 as seen along section line A-A.
Figure 13:
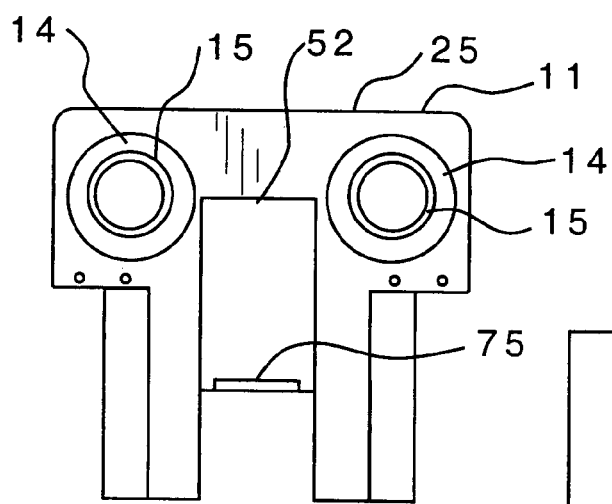
FIG. 13 is a view in front elevation of the upper plate portion of a third embodiment of the cervical compression plate assembly of the present invention.
Figure 15:
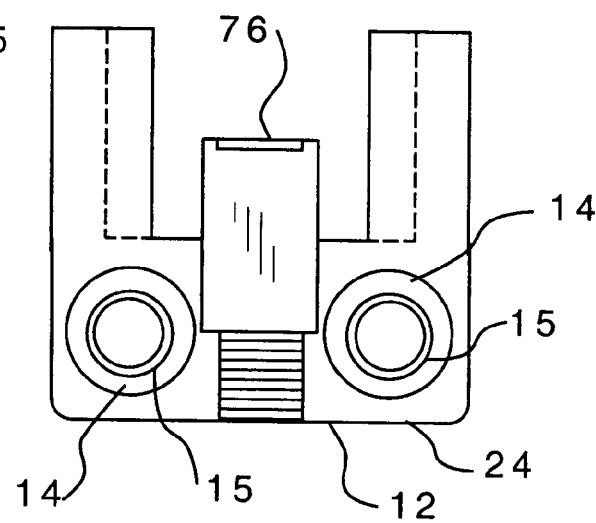
FIG. 15 is a view in front elevation of the bottom plate for combination with the upper plate shown in FIG. 13 to provide an alternate third embodiment of the cervical compression plate assembly of the present invention.
Figure 14:
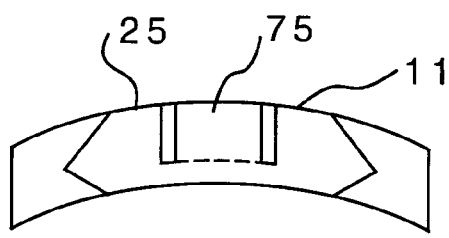
FIG. 14 is a bottom end view of the upper plate shown in FIG. 13.
Figure 16:
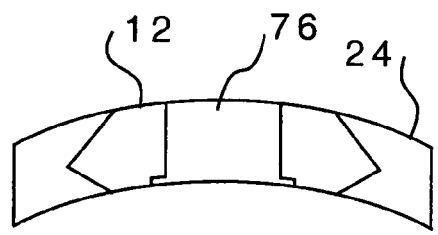
FIG. 16 is a top end view of the lower plate shown in FIG. 15.
Figure 17:
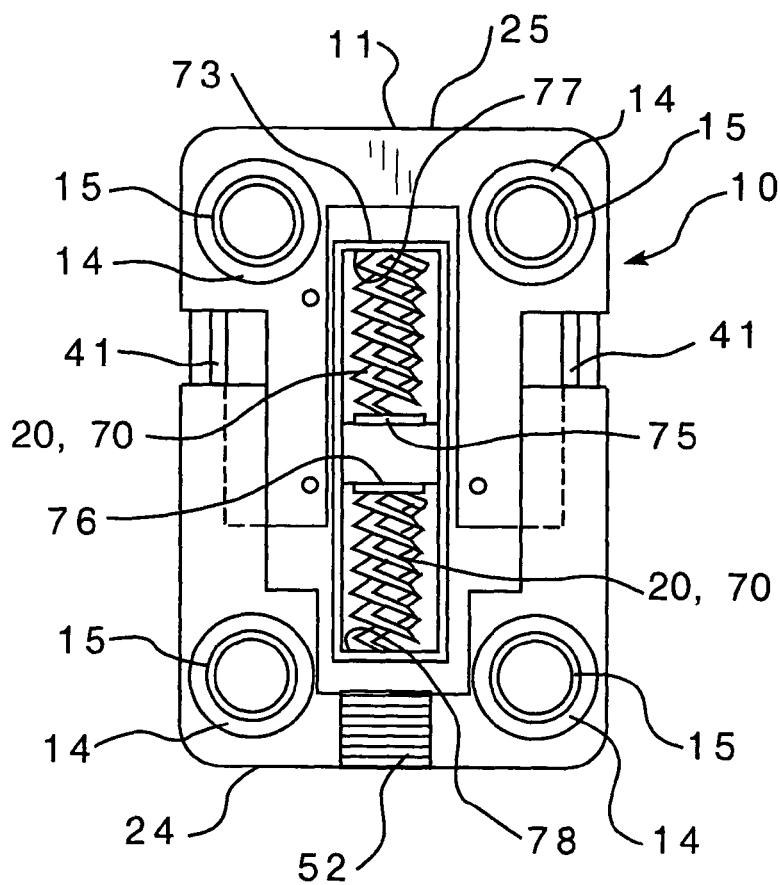
FIG. 17 is a view in front elevation illustrating the embodiment of FIGS. 13, 14, 15 and 16 in combined form.

Turning next to the embodiment of the present invention illustrated in FIGS. 6 though 12, the basic operation and application of the plate assembly 10 therein illustrated is identical to that of the embodiment illustrated in FIGS. 1 and 2. The primary difference in this embodiment is that the spring means 20 is provided in the form of multiple coil tension springs 50 instead of a tension wire 21. Also, the mechanism in this embodiment to prevent the distance from increasing between upper and lower screw receiving elements 11 and 12 is provided in the form of a ratchet and pawl mechanism 51 which includes a washboard rack 52 provided in upper plate 25 and a flexible pawl 53 secured to lower plate 24. The pawl 53 is provided with an inwardly protruding lip 54 which engages between the ratchet teeth of rack 52. The teeth of rack 52 are so designed whereby the distance between screw receiving elements 11 and 12 may decrease but may not increase as the pawl 53 will slide over the teeth of rack 52 as the upper and lower plates 25 and 24 are compressed toward each other, but will grip the backsides of these teeth and prevent any separation thereof. As an alternative pawl 52 may be provided as an integral part of lower plate 24.

Four coil tension springs 50 are provided in this embodiment with two springs being housed on each side of the assembly 10 in respective spring compartments 55 an 56 provided within assembly 10. Opposite ends of stretch springs 50 are secured to the respective upper and lower plates 25 and 24 with pins 57. Upper and lower plates 25 and 24 slide longitudinally relative to each other as provided by the dove tail slide arrangement 58 which includes the dove tail male portion 59 of upper plate 25 and the corresponding receiving female dove tail portion 60 provided in lower plate 24.

Each of the springs 50 can generate approximately two pounds of force under tension and therefore combined generate approximately eight pounds of force. Cover plates (not shown) may be provided to fully cover exterior exposure of the springs 50 to protect surrounding soft tissue from becoming involved in the springs.

The embodiment of FIGS. 13 through 19 again operate and functions in the same manner as the plate assembly shown in the two previous embodiments. The primary modification of this embodiment is the incorporation of compression springs 70 for the spring means 20. Here the springs 70 are illustrated as wire coiled compression springs. Of course, they may be substituted with other compression devices such as fluid pistons, fluid compression chambers or resilient polymeric foams. This embodiment is actually preferred for construction purposes as the compression springs 70 do not require physical opposite end securement to the assembly 10 as is specifically required for the tension spring members provided in the first two embodiments.

In this embodiment, the upper and lower plates 25 and 24 have a longitudinal slide mechanism which incorporates a pair of male protrusions 71 in the upper plate 25 and a pair of corresponding female receiving slide portions 72 in lower plate 23.

Also, in this embodiment the respective spring compartments 55 and 56 are provided by a continuous floating rectangular spring retaining band 73 which entirely surrounds both spring compartments 55 and 56. Upper plate 25 is provided with an outwardly protruding spring end retaining lip 75 and lower plate 24 is provided with outwardly protruding spring retaining lip 76. Accordingly, upper spring 70 is retained under compression between the upper end 77 of rectangular spring retaining band 73 and lip 75. Similarly, lower compression spring 70 is retained under compression between the lower end 78 of band 73 and the outwardly protruding lip 76. With this arrangement it will be observed that compression springs 70 continuously urge screw receiving elements 11 and 12 to converge towards each other.

Figure 18:
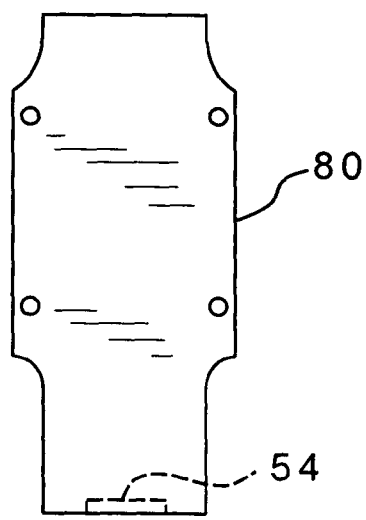
FIG. 18 is a view in front elevation of a cover plate to be applied to the assembly shown in FIG. 17.
Figure 19:
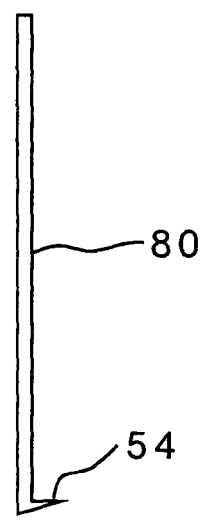
FIG. 19 is a view in right side elevation of the cover plate shown in FIG. 18.

The spring compartments 55 and 56, together with the band 73 and protrusions 75 and 76, are covered with cover plate 80 shown in FIGS. 18 and 19. In this embodiment the protruding pawl 54 for the ratchet mechanism 51 is provided as a part of cover plate 80 for engaging the washboard ratchet rack 52.

The embodiment of FIGS. 20 through 23 is similarly constructed and operates in the same manner as the embodiment shown in FIGS. 13 through 19 and operates through the use of compression springs 70 in the same manner. The primary difference of this latter embodiment is that the plate assembly 10 is a two level plate design. This design permits securement of cervical vertebrae at two different levels since there are three plates, upper plate 25, lower plate 24 and middle plate 85 which all slide longitudinally with respect to each other to permit application of compression loads between upper plate 25 and middle plate 85 and also between lower plate 24 and middle plate 85 in the same manner as described with respect to the immediately preceding embodiment.

In this embodiment, the spring retaining band 73 is configured differently to accommodate the three plates. In this embodiment, two separate bands 73 respectively enclose spring compartments 55 and 56 at opposite ends of the assembly 10 and then a portion thereof extends into the interior spring chambers 86 and 87 to further engage one of the two compression springs 70 contained therein. In addition, center plate 85 is also provided with two protruding spring end retaining lips 90 and 91. Accordingly, the upper band 73 herein designated as band 93 engages the two compression springs 94 within compartment 55 and also engages the spring 94 within spring compartment 86. This combined mechanism, as with the previous embodiment, works to continuously urge upper plate 25 and middle plate 85 to slidably converge or slide toward each other.

In the same fashion, the lower band 73, herein designated as band 100 encloses and engages springs 101 in compartment 56 and compression spring 101 in compartment 87 of the middle plate. This combination accordingly continuously urges middle plate 85 and bottom plate 24 continuously toward each other under the force as supplied by compression springs 101.

Figure 24:
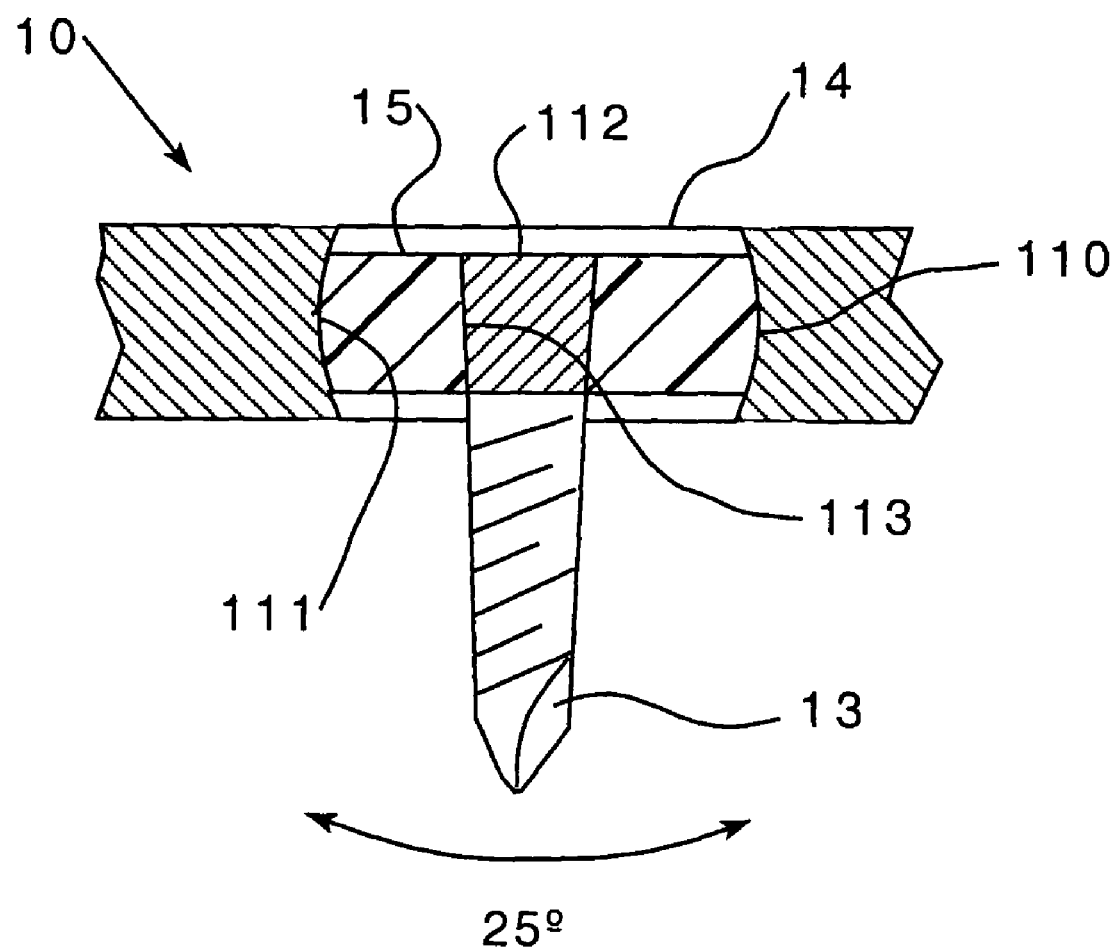
FIG. 24 is an enlarged schematic view with portions shown in vertical mid cross section illustrating an alternative embodiment of the pressure fit bushing ring utilized in the plate assembly of the present invention to affix the attitude of the bone fixation screws relative to the plate assembly.

Referring next to FIG. 24, an alternative embodiment of the pressure fit bushing ring 15 is illustrated for locking the self tapping bone fixations screws 13 at different angled attitudes relative to the plate assembly 10. In this embodiment, the pressure fit bushing ring 15 is not a part of, or rigidly secured to, the plate assembly 10. Instead, it is provided with a rounded convex perimeter contour 110 which mates an annular concave seat 111 of screw head seats 14. The shank of screw 13 is provided with a tapered roughened head 112 which fully engages and expands the internal pressure fit passage 113 of bushing ring 15 when the screw 13 is fully seated and engaged.

The tapered diameter of head 112 causes ring 15 to expand uniformly in the outward direction as the ring 15 is made of a somewhat resilient material. This expansion in turn causes the outer contours 110 of bushing 15 to tightly engage the mating interior contours 111 of seat 14 in plate assembly 10. The result is that screw 13 is originally retained at its original angle of insertion relative to plate assembly 10.

I claim:

1. A cervical compression plate assembly having screw receiving elements at opposite ends thereof configured for engaging bone fixation screws extending from respective vertebral elements, means for permitting the distance between said screw receiving elements at opposite ends to be shortened but preventing said distance from increasing; the improvement comprising compression spring means housed in said assembly and configured for continuously urging said screw receiving elements at opposite ends together for thereby providing continuous compressive loading on bone graft material disposed between the vertebral elements.

2. The cervical compression plate assembly of claim 1, including a screw locking mechanism for locking said screws to said plate assembly.

3. The cervical compression plate assembly of claim 2, wherein said screw receiving elements include screw head seats configured for seating the heads of the bone fixation screws at different attitudes.

4. The cervical compression plate assembly of claim 3, wherein said screw locking mechanism includes pressure fit rings in said screw receiving elements for engaging and locking self tapping threaded shanks of said screws in preselected angles of attitude.

5. The cervical compression plate assembly of claim 1, wherein said compression spring means includes a tension spring.

6. The cervical compression plate assembly of claim 5, wherein said tension spring is a wire under tension.

7. The cervical compression plate assembly of claim 6, including a tension torque drive for adjusting the tension applied to said wire.

8. The cervical compression plate assembly of claim 1, wherein said compression spring means includes a compression spring.

9. The cervical compression plate assembly of claim 1, including a removable spacer disposed between said screw receiving elements at opposite ends for initially preventing the distance between said screw receiving elements at opposite ends from being shortened by said compression spring means before application of said plate assembly.

10. A cervical compression plate assembly:
including first and second elongate plates slidably received with respect to each other in their longitudinal direction for adjustably changing the distance between opposite ends of said plate assembly, said opposite ends configured for respective attachment to first and second vertebra with the aid of bone fixation screws and a lock assembly for locking said first and second plates from further relative distraction therebetween;
and means for permitting the distance between said opposite ends to be shortened;
the improvement comprising:
compression spring means received in said plate assembly and configured for urging said opposite ends together for thereby providing continuous compressive loading.

11. The cervical compression plate assembly of claim 10, including a screw locking mechanism for locking said screws to said plate assembly.

12. The cervical compression plate assembly of claim 11, wherein said screw receiving elements include screw head seats configured for seating the heads of the bone fixation screws at different attitudes.

13. The cervical compression plate assembly of claim 12, wherein said screw locking mechanism includes pressure fit rings in said screw receiving elements for engaging and locking self tapping threaded shanks of said screws in preselected angles of attitude.

14. The cervical compression plate assembly of claim 10, wherein said compression spring means includes a tension spring.

15. The cervical compression plate assembly of claim 14, wherein said tension spring is a wire under tension.

16. The cervical compression plate assembly of claim 15, including a tension torque drive for adjusting the tension applied to said wire.

17. The cervical compression plate assembly of claim 10, wherein said compression spring means includes a compression spring.

18. The cervical compression plate assembly of claim 10, including a removable spacer disposed between said opposite ends for initially preventing the distance between said opposite ends from being shortened by said compression spring means before application of said plate assembly.

* * * * *